United States Patent
Lumauig (10) Patent No.: US 9,737,368 B2
(45) Date of Patent: Aug. 22, 2017

(54) SYSTEM AND METHOD FOR ATTACHING A RADIOPAQUE MARKER BEAD TO AN ENDOPROSTHESIS

(71) Applicant: Abbott Cardiovascular Systems Inc., Santa Clara, CA (US)

(72) Inventor: Rommel Lumauig, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 165 days.

(21) Appl. No.: 14/629,669

(22) Filed: Feb. 24, 2015

(65) Prior Publication Data

US 2016/0242851 A1  Aug. 25, 2016

(51) Int. Cl.
| | |
|---|---|
| *A61F 2/06* | (2013.01) |
| *A61B 19/00* | (2006.01) |
| *A61F 2/82* | (2013.01) |
| *B25B 11/00* | (2006.01) |

(Continued)

(52) U.S. Cl.
CPC ............... *A61B 19/54* (2013.01); *A61F 2/82* (2013.01); *B23P 19/02* (2013.01); *B25B 11/00* (2013.01); *A61B 2019/5466* (2013.01); *A61B 2090/3966* (2016.02); *A61F 2220/0033* (2013.01);
(Continued)

(58) Field of Classification Search
CPC ............ A61B 19/54; A61B 2090/3966; A61B 2019/5466; A61B 90/39; A61F 2/82; A61F 2220/0033; A61F 2220/0041; A61F 2240/00; A61F 2250/0098; A61F 2/07; A61F 2/86; A61F 2/91; B25B 11/00; B23P 19/02

See application file for complete search history.

(56) References Cited

U.S. PATENT DOCUMENTS

| | | |
|---|---|---|
| 3,068,563 A | 12/1962 | Reverman |
| 4,361,948 A | 12/1982 | Omata |
| 5,302,694 A | 4/1994 | Buchholz |

(Continued)

FOREIGN PATENT DOCUMENTS

| | | |
|---|---|---|
| EP | 1 277 449 | 1/2003 |
| EP | 1 570 808 | 9/2005 |

(Continued)

OTHER PUBLICATIONS

International Search Report and Written Opinion mailed Jun. 23, 2016 in International Patent Application No. PCT/US2016/018773, 14 pages.

(Continued)

*Primary Examiner* — Jun Yoo (74) *Attorney, Agent, or Firm* — Squire Patton Boggs (US) LLP (57) ABSTRACT

A radiopaque marker bead can be attached to an endoprosthesis by pressing an end of bead into a through hole formed into the endoprosthesis and allowing the opposite end of the bead to pass through the hole and protrude out of the other end of the hole. Both ends of the bead can then be pressed and flattened so as to frictionally engage both ends of the hole. A support tool having a curved outer surface can be inserted into the endoprosthesis to support the endoprosthesis luminal surface while the bead is being pushed into the hole. The support tool has a depression which allows the opposite end of the bead to protrude out of the hole.

10 Claims, 9 Drawing Sheets

(51) Int. Cl.
*B23P 19/02* (2006.01)
*A61B 90/00* (2016.01)

(52) U.S. Cl.
CPC ... *A61F 2220/0041* (2013.01); *A61F 2240/00* (2013.01); *A61F 2250/0098* (2013.01)

(56) References Cited

U.S. PATENT DOCUMENTS

| | | | |
|---|---|---|---|
| 5,470,944 | A | 11/1995 | Bonsignore |
| 5,565,215 | A | 10/1996 | Greff et al. |
| 5,665,831 | A | 9/1997 | Neuenschwander et al. |
| 5,670,161 | A | 9/1997 | Healy et al. |
| 5,837,008 | A | 11/1998 | Berg et al. |
| 5,844,067 | A | 12/1998 | Erneta |
| 6,022,374 | A | 2/2000 | Imran |
| 6,334,871 | B1 | 1/2002 | Dor et al. |
| 6,464,720 | B2 | 10/2002 | Boatman et al. |
| 6,471,721 | B1 | 10/2002 | Dang |
| 6,506,437 | B1 | 1/2003 | Harish et al. |
| 6,641,607 | B1 | 11/2003 | Hossainy et al. |
| 6,673,106 | B2 | 1/2004 | Mitelberg et al. |
| 6,726,713 | B2 | 4/2004 | Schaldach et al. |
| 6,769,161 | B2 | 8/2004 | Brown et al. |
| 6,918,928 | B2 | 7/2005 | Wolinsky et al. |
| 6,926,733 | B2 | 8/2005 | Stinson |
| 9,532,888 | B2 * | 1/2017 | Dugan ............... A61F 2/82 |
| 2001/0027339 | A1 | 10/2001 | Boatman et al. |
| 2002/0143386 | A1 | 10/2002 | Davila et al. |
| 2002/0193862 | A1 | 12/2002 | Mitelberg et al. |
| 2003/0028241 | A1 | 2/2003 | Stinson |
| 2003/0069630 | A1 | 4/2003 | Burgermeister et al. |
| 2003/0150250 | A1 | 8/2003 | Shortt |
| 2004/0010306 | A1 | 1/2004 | Freyman et al. |
| 2004/0024449 | A1 | 2/2004 | Boyle |
| 2004/0088039 | A1 | 5/2004 | Lee et al. |
| 2004/0146546 | A1 | 7/2004 | Gravett et al. |
| 2004/0181236 | A1 | 9/2004 | Eidenschink et al. |
| 2004/0204750 | A1 | 10/2004 | Dinh |
| 2004/0236428 | A1 | 11/2004 | Burkinshaw et al. |
| 2005/0004653 | A1 | 1/2005 | Gerberding et al. |
| 2005/0015138 | A1 | 1/2005 | Schuessler et al. |
| 2005/0060025 | A1 | 3/2005 | Mackiewicz et al. |
| 2005/0106204 | A1 | 5/2005 | Hossainy et al. |
| 2005/0107865 | A1 | 5/2005 | Clifford et al. |
| 2005/0154450 | A1 | 7/2005 | Larson et al. |
| 2005/0175666 | A1 | 8/2005 | Ding |
| 2005/0233062 | A1 | 10/2005 | Hossainy et al. |
| 2005/0283228 | A1 | 12/2005 | Stanford |
| 2007/0043434 | A1 | 2/2007 | Meerkin et al. |
| 2007/0156230 | A1 | 7/2007 | Dugan et al. |
| 2007/0266542 | A1 | 11/2007 | Melsheimer |
| 2008/0015684 | A1 | 1/2008 | Wu |
| 2012/0035709 | A1 | 2/2012 | Young et al. |
| 2012/0144663 | A1 | 6/2012 | Wu |
| 2014/0013574 | A1 | 1/2014 | Giasolli |

FOREIGN PATENT DOCUMENTS

| | | |
|---|---|---|
| EP | 1 656 905 | 5/2006 |
| JP | 2002-233578 | 8/2002 |
| JP | 2004-358242 | 12/2004 |
| WO | WO 99/17817 | 4/1999 |
| WO | WO 02/26162 | 4/2002 |
| WO | WO 03/015664 | 2/2003 |
| WO | WO 03/047463 | 6/2003 |

OTHER PUBLICATIONS

U.S. Appl. No. 11/009,977, filed Dec. 9, 2004, Pacetti.
European Search Report for EP 13161281, mailed Jun. 3, 2014, 8 pgs.
International Search Report for PCT/US2006/049269, filed Dec. 21, 2006, mailed Jun. 15, 2007, 19 pgs.
International Search Report for PCT/US2007/015994, mailed Sep. 25, 2008, 4 pgs.
Translation of the Notice of Reasons for Rejection from JPO for appl. No. P2008-549504, dispatched Mar. 27, 2012, 4 pgs.
Ali et al. "Thermoplastic Interpenetrating Polymer Networks", Advances in Interpenetrating Polymer Networks vol. IV. Ed. D. Klempner et al. Lancaster: Technomic Publishing Company, Inc. 1994 p. 18.
Hennink et al., "Reflexive Polymers and Hydrogels", Ed. By Yui et al. Boca Raton: CRC Press LLC, p. 407 (2004).
Moses et al., "Sirolimus-Eluting Stents versus Standard Stents in Patients with Stenosis in a Native Coronary Artery", The New England Journal of Medicine 349, pp. 1315-1323 (2003).
Woo Lim et al., "Stereocomplex Formation between Enantiomeric PLA-PEG-PLA Triblock Copolymers: Characterization and Use as Protein-Delivery Micropratriculate Carriers", Journal of Applied Polymer Science 75, pp. 1615-1623 (2000).

* cited by examiner

SYSTEM AND METHOD FOR ATTACHING A RADIOPAQUE MARKER BEAD TO AN ENDOPROSTHESIS

FIELD

The invention relates, in general, to manufacturing of medical devices, more particularly, to manufacturing of an endoprosthesis.

BACKGROUND

An endoprosthesis is an artificial device that is placed inside the body, and more particularly, within an anatomical lumen. An anatomical lumen is a cavity of a tubular organ, examples of which include without limitation a urinary tract, bile duct, fallopian tube, esophagus, and arterial or venous vasculature. Stents are a type of endoprosthesis which are often used in the treatment of atherosclerotic stenosis in blood vessels. Stenosis refers to a narrowing or constriction of the diameter of an anatomical lumen or orifice. Stents can reinforce the walls of the anatomical lumen and prevent a reoccurrence of stenosis.

The process of locating a region that may require treatment with an endoprosthesis often involves obtaining an x-ray image of an anatomical lumen. A contrast agent, which contains a radiopaque substance such as iodine is injected into the anatomical lumen. "Radiopaque" refers to the ability of a substance to absorb x-rays. The x-ray image allows a physician to identify a potential treatment region at which a stent can be delivered and deployed. Delivery involves transporting the stent through the anatomical lumen, which can be tortuous and require the stent to bend in order to pass through sharp bends. Deployment involves expanding the stent within the treatment region so that it engages and supports the walls of the anatomical lumen.

In addition to meeting the mechanical requirements for delivery and deployment, it is desirable for a stent to be radiopaque, or fluoroscopically visible under x-rays. Accurate stent placement is facilitated by real time visualization of the stent during delivery and deployment to allow for precise placement. This can be accomplished by fluoroscopy or similar x-ray visualization procedures. For a stent to be fluoroscopically visible it must be more absorptive of x-rays than the surrounding tissue.

Stents made of bioresorbable polymers have been developed to allow for improved healing of the anatomical lumen. Examples of bioresorbable polymer stents include those described in U.S. Pat. No. 8,002,817 to Limon, U.S. Pat. No. 8,303,644 to Lord, and U.S. Pat. No. 8,388,673 to Yang, which are incorporated herein by reference. As used herein, "bioresorbable" refers to a material capable being completely eroded, degraded (either biodegraded and/or chemically degraded), and/or absorbed when exposed to bodily fluids (such as blood or other fluid); and can be gradually resorbed, absorbed and/or eliminated by the body. Other terms such as biodegradable, bioabsorbable, and bioerodible may be found in the literature, and while these terms have specific definitions, they are often used interchangeably. The term "biostable" refers to a material that is not bioresorbable.

A drawback of bioresorbable polymers (and polymers generally composed of carbon, hydrogen, oxygen, and nitrogen) is that they are radiolucent with no radiopacity. Biodegradable polymers tend to have x-ray absorption similar to body tissue. This is addressed by attaching radiopaque markers to structural elements of the stent. Attachment entails a number of challenges. First, radiopaque markers are often very tiny which makes insertion into a stent difficult. Second, polymeric stent struts undergo significant deformation during delivery and deployment, during which the radiopaque marker must remain attached to the stent. Although the use bioresorbable materials typically means that material thicknesses are greater than those required of metals, improvements in bioresorbable stent design and manufacturing are allowing for stent struts with reduced thickness. For example, the thickness of a bioresorbable stent strut could be as low as 0.003 inch (0.075 mm). With reduced thickness, there is less volume in the stent strut to ensure that the radiopaque marker remains in place. Thus, it is important to maximize engagement between the radiopaque marker and the endoprosthesis.

Accordingly there is a continuing need to for a system and method of attaching radiopaque markers to help maximize engagement to the endoprosthesis. Also, there is a continuing need to for a system and method of attaching radiopaque markers with greater efficacy and uniformity.

SUMMARY

Briefly and in general terms, the present invention is directed to a system and method for attaching a radiopaque marker bead to an endoprosthesis. The present invention is also directed to an endoprosthesis to which a radiopaque marker bead has been attached.

In aspects of the present invention, a system comprises a pusher tool including a pusher outer surface configured to push a radiopaque marker bead into a hole formed through an abluminal surface of an endoprosthesis, and a support tool including a curved outer surface configured to support a luminal surface of the endoprosthesis adjacent to the hole, there being a depression formed into the curved outer surface. A first imaginary plane intersecting the depression defines a first width of the depression and a first radial depth of the depression, the first width is from 0.003 inch to 0.020 inch, the first radial depth is from 0.002 inch to 0.019 inch, and the first width is greater than the first radial depth.

In aspects of the present invention, a method comprises: positioning a radiopaque marker bead adjacent to an endoprosthesis such that a first portion and a second portion of the radiopaque marker bead are disposed over a hole formed through an abluminal surface of an endoprosthesis; after positioning, pressing the first portion of the radiopaque marker bead into the hole until the second portion of the radiopaque marker bead moves out of the hole and protrudes from a luminal surface of the endoprosthesis; and after pressing the first portion, pressing the second portion of the marker into the hole.

In aspects of the present invention, an endoprosthesis comprises: a stent structure including a core substrate formed of a bioabsorbable polymer material, there being a through hole formed through the core substrate, the through hole having a diameter of 0.005 inch to 0.025 inch; and a radiopaque marker bead including a first portion deformed into contact with a wall of an abluminal end segment of the through hole and a second portion deformed into contact with a wall of a luminal end segment of the through hole.

The features and advantages of the invention will be more readily understood from the following detailed description which should be read in conjunction with the accompanying drawings.

DETAILED DESCRIPTION OF EXEMPLARY EMBODIMENTS

As used herein, "abluminal surface" refers to a radially outward facing surface.

As used herein, "luminal surface" refers to a radially inward facing surface.

Figure 1:
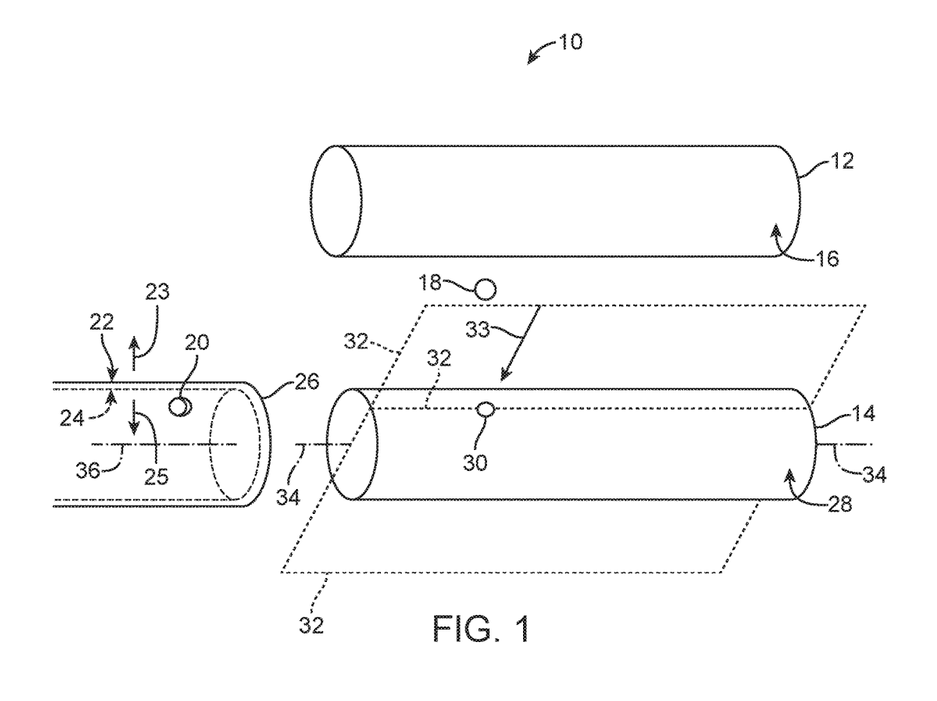
FIG. 1 is an isometric, exploded view showing an exemplary system for attaching a radiopaque marker bead to an exemplary endoprosthesis, and showing an axial imaginary plane intersecting a depression in a support tool.

Referring now in more detail to the exemplary drawings for purposes of illustrating aspects of the invention, wherein like reference numerals designate corresponding or like elements among the several views, there is shown in FIG. 1 exemplary system 10 for attaching a radiopaque marker bead to an endoprosthesis. System 10 comprises pusher tool 12 and support tool 14. Pusher tool 12 includes pusher outer surface 16 configured to push radiopaque marker bead 18 into hole 20 formed through abluminal surface 22 of endoprosthesis 26. Hole 20 is a through hole that extends through abluminal surface 22 and luminal surface 24 of endoprosthesis 26. Support tool 14 includes curved outer surface 28 which is configured to support portions of luminal surface 24 adjacent to hole 20. Depression 30 is formed into curved outer surface 28 of support tool 14.

Figure 18A:
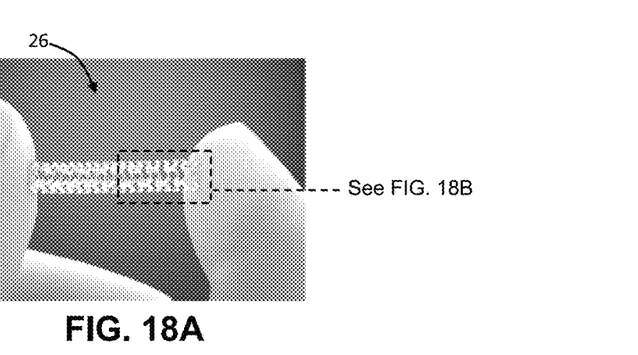
FIGS. 18A and 18B are photographs of an exemplary stent.
Figure 18B:
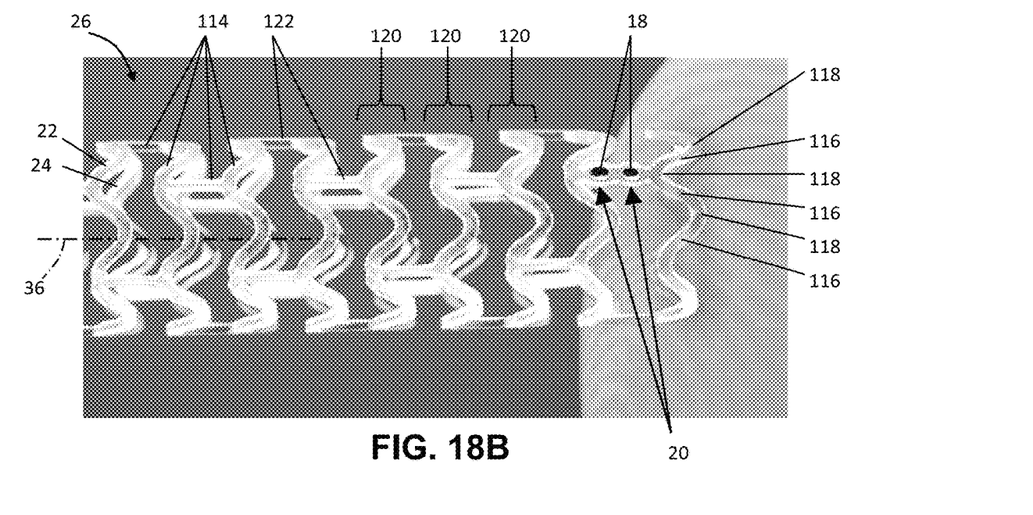

Endoprosthesis 26 is illustrated schematically as a hollow tube with solid walls that define abluminal surface 22 and luminal surface 24. Abluminal surface 22 faces radially outward in the direction of arrow 23. Luminal surface 24 faces radially inward in the direction of arrow 25. Endoprosthesis 26 can be a stent, graft tube, stent-graft, or medical device configured for implantation in the body of a patient. For example, endoprosthesis 26 can be a bioresorbable stent comprising interconnected stent struts, as shown in FIGS. 18A and 18B. The cross-sectional views of endoprosthesis 26 discussed below can represent a structural member, such as a stent strut.

System 10 can be used by inserting support tool 14 into endoprosthesis 26 to provide support for luminal surface 24 while pusher tool 12 presses radiopaque marker bead 18 into hole 20. As will be discussed below, depression 30 in support tool 14 can improve insertion of radiopaque marker bead 18 into hole 20 of endoprosthesis 26.

First imaginary plane 32 intersects depression 30. Plane 32 is an axial imaginary plane that is coincident with longitudinal central axis 34 of support tool 14 and/or longitudinal central axis 36 of endoprosthesis 26. Longitudinal central axis 34 and/or longitudinal central axis 36 lie in plane 32.

Figure 2:
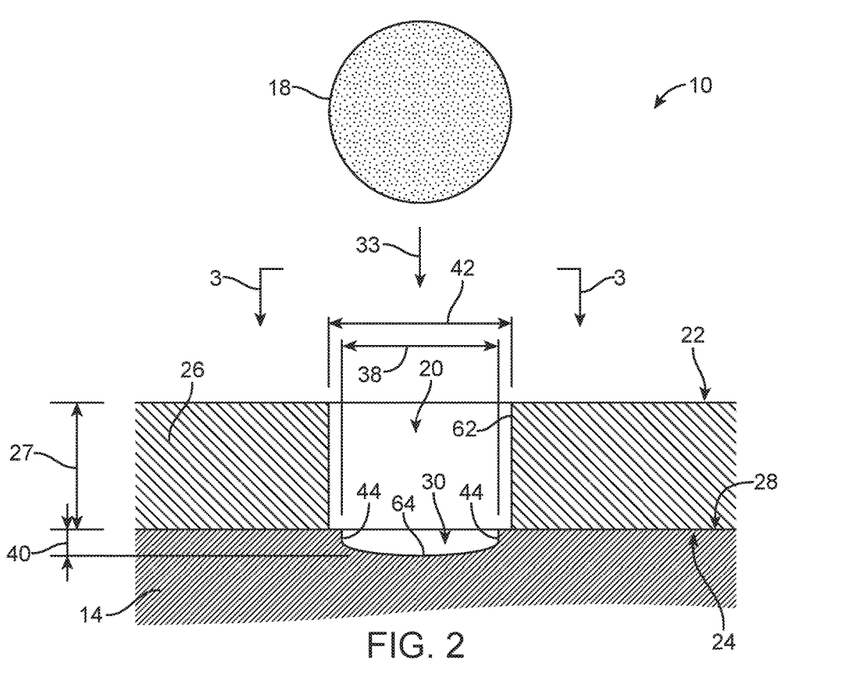
FIG. 2 is a fragmentary cross-section view at the axial imaginary plane, showing the support tool of the system of FIG. 1 supporting the endoprosthesis prior to insertion of the radiopaque marker bead into a hole in the endoprosthesis.

FIG. 2 shows a cross-section of depression 30 at first imaginary plane 32 after support tool 14 has been inserted into endoprosthesis 26. What is shown for endoprosthesis 26 is the core material or substrate of the medical device without a superficial coating (such as a drug-containing coating) which could be applied at a later time during the manufacturing process. The core substrate bears all or most of the mechanical load which is experienced by endoprosthesis within the body of the patient. Without the core substrate, the endoprosthesis would collapse within the body of the patient. Radial thickness 27 of the core substrate adjacent hole 20 can be from 0.002 inch to 0.01 inch (0.05 to 0.25 mm), or from 0.003 inch to 0.007 inch (0.07 to 0.18 mm), or from 0.003 inch to 0.005 inch (0.07 to 0.13 mm). Other dimensions are possible depending on the type of endoprosthesis.

Figure 3:
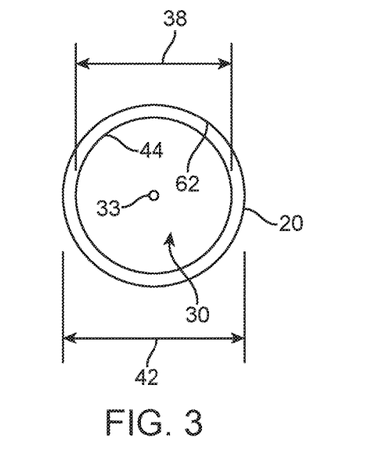
FIG. 3 is a plan view along line 3-3 in FIG. 2, showing the depression in the support tool in relation to the hole in the endoprosthesis.

FIG. 3 shows the plan view along line 3-3 in FIG. 2. As used herein, a "plan view" refers to a view looking down from directly above the subject. FIG. 3 shows a view of hole 20 and depression 30 when looking down arrow 33 (FIGS. 1 and 2). Arrow 33 is on an imaginary line which is located in first imaginary plane 32 and which passes through depression 30.

First imaginary plane 32 defines first width 38 of depression 30 and first radial depth 40 of depression 30. First width 38 is greater than first radial depth 40. Hole 20 in endoprosthesis 26 has diameter 42 that is greater than first width 38 of depression 30. Depression 30 includes wall 44 that forms a circle. First width 38 of depression 30 is the diameter of the circle formed by wall 44. First width 38 can be from 0.003 inch to 0.020 inch (0.07 to 0.51 mm). First radial depth 40 can be from 0.002 inch to 0.019 inch (0.05 to 0.50 mm). As a further example, hole 20 can have a diameter of 0.009 inch (0.23 mm) while first width 38 can be approximately 0.006 inch (0.15 mm) and radial depth can be from 0.002 inch (0.05 mm) to 0.004 inch (0.10 mm). With respect to numerical dimensions, the term "approximately" refers to a tolerance of plus and minus 10%.

Other dimensions are possible depending on the type of endoprosthesis.

FIGS. 4A-4F show an exemplary chronological sequence of views, each of which is a cross-section of depression 30 on first imaginary plane 32 after support tool 14 has been inserted into endoprosthesis 26. The sequence of views illustrates an exemplary method, according to aspects of the invention, for attaching radiopaque marker bead 18 to endoprosthesis 26. The method allows radiopaque marker bead 18 to engage abluminal end segment 46 and luminal end segment 48 of hole 20. Abluminal end segment 46 and luminal end segment 48 are at opposite ends of hole 20. Engagement of both end segments 46 and 48 of hole 20 can be preferable in that radiopaque marker bead 18 would be expected to have a decreased chance of become dislodged and separated from endoprosthesis 26 as compared when radiopaque marker bead 18 is engaged with only one end segment of hole 20.

Figure 4A:
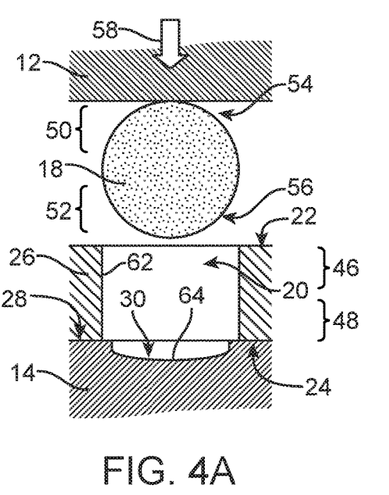
FIGS. 4A-4F are fragmentary cross-section views showing insertion of the radiopaque marker bead into the endoprosthesis.

As shown in FIG. 4A, radiopaque marker bead 18 is positioned adjacent to endoprosthesis 26 such that first portion 50 and second portion 52 of radiopaque marker bead 18 are disposed over hole 20 formed through abluminal surface 22 of endoprosthesis 26. First portion 50 and second portion 52 are at opposite ends of radiopaque marker bead 18. At this stage, radiopaque marker bead 18 is round. For example, radiopaque marker bead 18 can be in the shape of a sphere, oval, or other round shape. Due to the round shape of radiopaque marker bead 18, outer surface 54 of first portion 50 and outer surface 56 of second portion 52 are curved and not flat.

Depression 30 is radially aligned with hole 20. Curved outer surface 28 of support tool 14 supports luminal surface 24 of endoprosthesis 26 to help prevent the possibility that portions of endoprosthesis 26 adjacent to hole 20 might collapse or give way during insertion of radiopaque marker bead 18 into hole 20.

Figure 4B:
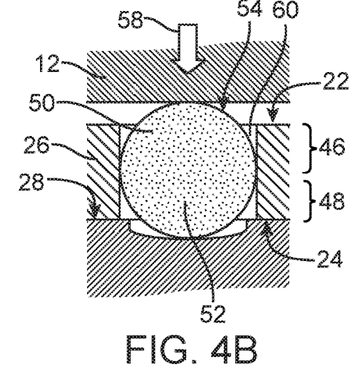

Next, as shown in FIG. 4B, first portion 50 of radiopaque marker bead 18 is pressed by pusher tool 12 into hole 20 until second portion 52 of radiopaque marker bead 18 moves out of hole 20 and protrudes from luminal surface 24 of endoprosthesis 26. Pusher tool 12 pushes radiopaque marker bead 18 in a radial inward direction indicated by arrow 58. The radially inward direction can be perpendicular to longitudinal central axis 36 (FIG. 1) of endoprosthesis 26. Pushing the radiopaque marker bead can also be accomplished by rolling pusher tool 12 over the curved abluminal surface 22 of endoprosthesis 26, which results in a downward force applied to radiopaque marker bead 18 in the direction of arrow 58.

Curved outer surface 28 of support tool 14 continues to support luminal surface 24 of endoprosthesis 26 while first portion 50 of radiopaque marker bead 18 is pressed by pusher tool 12. Depression 30 in curved outer surface 28 of support tool 14 receives second portion 52 of radiopaque marker bead 18. Radial depth 40 (FIG. 2) limits travel of second portion 52 out of hole 20.

Because radiopaque marker bead 18 is made of a relatively soft and malleable material, radiopaque marker bead 18 may pile up or accumulate at abluminal end segment 46 of hole 20 before radiopaque marker bead 18 can adequately enter hole 20 to allow for engagement with luminal end segment 48 of hole 20. Without being limited to a theory of operation, it is believed that allowing second portion 52 of radiopaque marker bead 18 to move slightly out of hole 20, as shown in FIG. 4B, facilitates adequate entry of first portion 50 into hole 20.

Pressing first portion 50 may cause some deformation of radiopaque marker bead 18, although radiopaque marker bead 18 is illustrated in FIG. 4B with same shape as in FIG. 4A. Radiopaque marker bead 18 could, at least partially, maintain its round shape when it enters hole 20 of endoprosthesis 26. Due to the round shape radiopaque marker bead 18, outer surface 54 of first portion 50 of radiopaque marker bead 18 may protrude from abluminal surface 22 of endoprosthesis 26, as shown in FIG. 4B, and air gap 60 may exist between outer surface 54 and wall 62 (FIG. 4A) of hole 20. In FIG. 4B, abluminal end segment 46 of hole 20 is not filled by radiopaque marker bead 18.

Figure 4C:
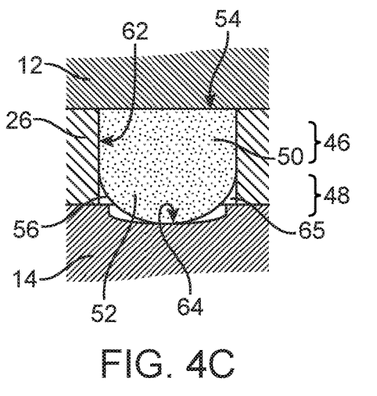
Figure 5:
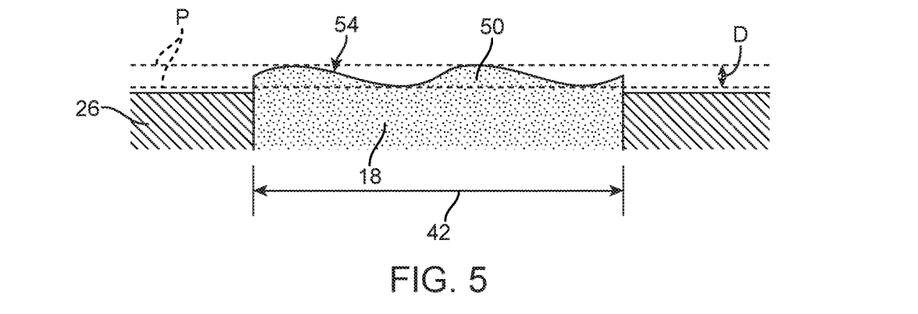
FIG. 5 is a fragmentary cross-section view showing a flattened surface of the radiopaque marker bead after it has been pressed into the endoprosthesis.

In FIG. 4C, pressing of first portion 50 of radiopaque marker bead 18 results in flattening of outer surface 54 of first portion 50 of radiopaque marker bead 18. The terms "flattening" and "flat" as applied to radiopaque marker bead 18 means that the curved surface of radiopaque marker bead 18 becomes flat with a flatness tolerance of 10% of diameter 42 of hole 20. As shown in FIG. 5, the flatness tolerance of 10% means that the visible portion of outer surface 54 of first portion 50 of radiopaque marker bead 18 must lie between two imaginary planes P that are spaced part by a distance D that is no more than 10% of diameter 42 of hole 20.

Pressing of first portion 50 of radiopaque marker bead 18 also results in filling in of abluminal end segment 46 of the hole with first portion 50. The malleable material of radiopaque marker bead 18 fills in air gap 60 (FIG. 4B) and exerts pressure on wall 62 of hole 20, which can allow for greater frictional engagement between radiopaque marker bead 18 and abluminal end segment 46 of hole 20. As indicated above, radial depth 40 (FIG. 2) of depression 30 limits travel of second portion 52 out of hole 20. The position of bottom surface 64 of depression 30, as defined by radial depth 40 (FIG. 2), is selected such that radiopaque marker bead 18 will resist further movement so that pusher tool 12 causes first portion 50 to flatten and engage abluminal end segment 46 of hole 20. After second portion 52 of radiopaque marker bead 18 protrudes from luminal surface 24 of endoprosthesis 26, air gap 65 may exist between outer surface 56 of second portion 52 and wall 62 of hole 20. In FIG. 4C, luminal end segment 48 is not filled by radiopaque marker bead 18.

As discussed above, pressing of first portion 50 of radiopaque marker bead 18 results in deformation of marker bead 18. Radiopaque marker bead 18 may exert pressure on wall 62 at abluminal end segment 46 of hole 20. In some aspects, the pressure may deform wall 62 slightly. The process of pressing first portion 50 of radiopaque marker bead 18 can be referred to as a swaging process due to deformation and change in dimension of radiopaque marker bead 18 and/or hole 20.

After pressing of first portion 50 of radiopaque marker bead 18, support tool 14 is optionally rotated about its longitudinal central axis 34 (FIG. 1) and/or longitudinal central axis 36 of endoprosthesis 26. Rotation of support tool 14 can be performed so that second portion 52 of radiopaque marker bead 18 is pressed into and fills luminal end segment 48 of hole 20.

Figure 4D:
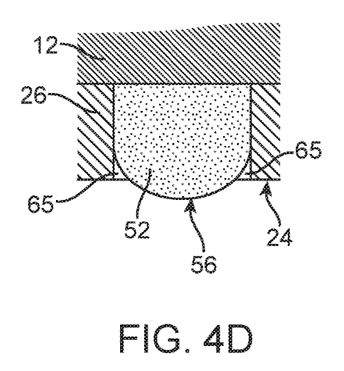
Figure 4E:
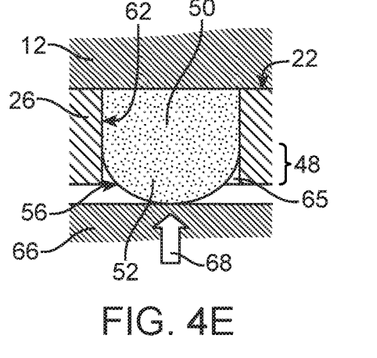

In further aspects, as shown in FIG. 4D, support tool 14 is removed from endoprosthesis 26. Removal can be performed by axially sliding support tool 14 along luminal surface 24 of endoprosthesis 26. Depending on the shape of depression 30 in support tool 14, sliding support tool 14 along luminal surface 24 of endoprosthesis 26 may press second portion 52 of radiopaque marker bead 18 and result in flattening of second portion 52 of radiopaque marker bead 18. In some aspects, removal of support tool 14 from endoprosthesis 26 does not flatten or only partially flattens second portion 52, and second portion 52 still protrudes from luminal surface 24 of endoprosthesis 26, as shown in FIG. 4D In FIG. 4E, after pressing first portion 50 and removal of support tool 14 from endoprosthesis 26, tool 66 is optionally inserted into endoprosthesis 26 and presses second portion 52 of radiopaque marker bead 18 into hole 20. Tool 66 pushes radiopaque marker bead 18 in a radial outward direction indicated by arrow 68. The radially outward direction can be perpendicular to longitudinal central axis 36 (FIG. 1) of endoprosthesis 26.

Pressing second portion 52 of radiopaque marker bead 18 (by rotation of support tool 14 and/or use of tool 66) results in flattening of outer surface 56 of second portion 52. Also, pressing second portion 52 results in filling of luminal end segment 48 of hole 20 with second portion 52. The malleable material of radiopaque marker bead 18 fills in air gap 65 (FIG. 4E) and exerts pressure on wall 62 of hole 20, which can allow for greater frictional engagement between radiopaque marker bead 18 and luminal end segment 48 of hole 20. Optionally, when tool 66 presses second portion 52 of radiopaque marker bead 18, pusher tool 12 is pressed in contact with first portion 50 so as to prevent the possibility of first portion 50 from being pushed out of hole 20 and to encourage second portion 52 to flatten and engage luminal end segment 48 of hole 20.

In some aspects, pusher tool 12 is not needed when tool 66 presses second portion 52 of radiopaque marker bead 18. That is, pusher tool 12 is not pressed in contact with first portion 50 of radiopaque marker bead 18 when tool 66 presses second portion 52 of radiopaque marker bead 18.

In some aspects, tool 66 can be a portion of tool 14 without depression 30. Alternatively, tool 66 is separate and distinct from tool 14. For example, tool 66 can be pusher tool 12 which has been removed from abluminal surface 22 of endoprosthesis 26.

As discussed above, pressing of second portion 52 of radiopaque marker bead 18 results in deformation of marker bead 18. Radiopaque marker bead 18 may exert pressure on wall 62 at luminal end segment 48 of hole 20. In some aspects, the pressure may deform wall 62 slightly. The process of pressing of second portion 52 of radiopaque marker bead 18 can be referred to as a swaging process due to deformation and change in dimension of radiopaque marker bead 18 and/or hole 20.

Figure 4F:
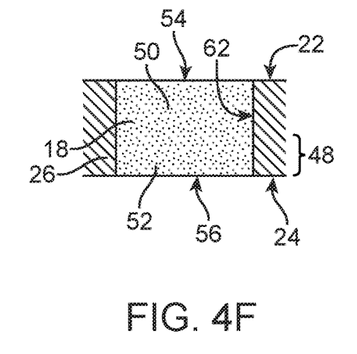

As shown in FIG. 4F, all tools have been removed from endoprosthesis 26 after second portion 52 has been pressed. Thereafter, endoprosthesis 26, together with radiopaque marker bead 18, can be subjected to additional manufacturing processes. Additional manufacturing processes include without limitation spraying endoprosthesis 26 with a coating that optionally contains a drug or other therapeutic agent, and mounting endoprosthesis 26 on a catheter. In cases where endoprosthesis 26 is a radially expandable stent, mounting can involve crimping the stent to a compressed state onto a catheter or other device used to deliver the stent into a location within the body of a patient.

Hole 20 in endoprosthesis 26 can be cylindrical. That is wall 62 can form a cylinder. When radiopaque marker bead 18, which may be spherical originally, is pressed from opposite ends as described above, radiopaque marker bead 18 deforms to fill the cylindrical space within hole 20, and radiopaque marker bead 18 takes the shape of a disc having opposite ends that are flat.

In FIG. 1, first imaginary plane 32 is an axial imaginary plane that extends in the same direction as longitudinal central axis 34 of support tool 14, as previously discussed, and the views of FIGS. 4A-4F are cross-sections of depression 30 at that axial imaginary plane. In other aspects, the first imaginary plane can extend in other directions, such as shown in FIG. 6.

Figure 6:
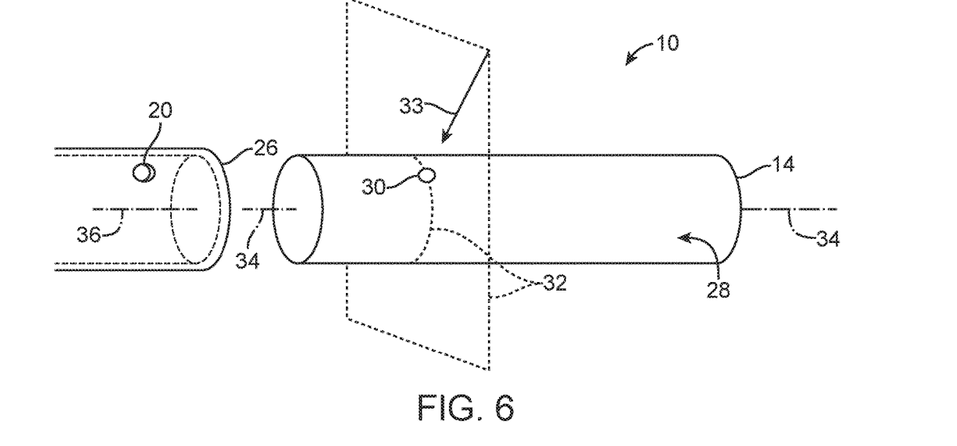
FIG. 6 is an isometric, exploded view of the system of FIG. 1, showing a transverse imaginary plane intersecting the depression in the support tool.
Figure 7:
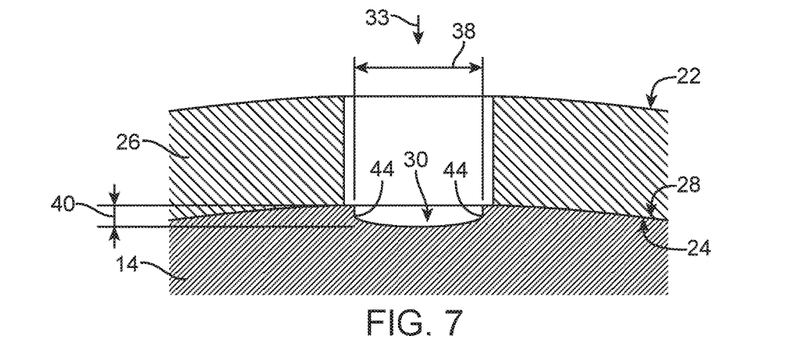
FIG. 7 is a fragmentary cross-section view at the transverse imaginary plane of FIG. 6 and showing the support tool of FIG. 1 supporting the endoprosthesis prior to insertion of the radiopaque marker bead.

In FIG. 6, first imaginary plane 32 is a transverse imaginary plane that is perpendicular to longitudinal central axis 34 of support tool 14 and/or longitudinal central axis 36 of endoprosthesis 26. Longitudinal central axis 34 and/or longitudinal central axis 36 is/are oriented normal to transverse imaginary plane 32. FIG. 7 is an exemplary cross-section at transverse imaginary plane 32 of FIG. 6. FIG. 7 shows depression 30 of support tool 14 after support tool 14 has been inserted into endoprosthesis 26.

In aspects of the invention, curved outer surface 28 of support tool 14 conforms to the contours of luminal surface 24. In further aspects of the invention, curved outer surface 28 of support tool 14 forms a cylinder or a partial cylinder having a radius of curvature less than the radius of curvature of luminal surface 24 of endoprosthesis 26. This allows for insertion of support tool 14 into endoprosthesis 26. In further aspects, the radius of curvature of curved outer surface 28 of support tool 14 is the same as that of luminal surface 24 of endoprosthesis 26. This allows for maximum support of luminal surface 24 so as to avoid damage or undue deformation of endoprosthesis 26 during insertion of radiopaque marker bead 18. In other aspects, the radius of curvature of curved outer surface 28 is up to 5%, up to 10% or up to 20% less than the radius of curvature of luminal surface 24 of endoprosthesis 26. This allows for ease of insertion of support tool 14 into endoprosthesis 26 while still providing support of luminal surface 24 adjacent to hole 20.

In FIG. 7, first imaginary plane 32 (a transverse imaginary plane in this aspect) defines first width 38 of depression 30 and first radial depth 40 of depression 30 in the same way as was previously described for the first imaginary plane of FIG. 2 (an axial imaginary in that previous aspect). In FIG. 7, first width 38 and radial depth 40 can have dimensions within the same ranges disclosed for FIGS. 2 and 3. First width 38 is greater than first radial depth 40. Depression 30 can be circular and rotationally symmetric around arrow 33 so that the cross-section views in transverse imaginary plane 32 are the same as what is shown in FIGS. 4A-4E.

Figure 8:
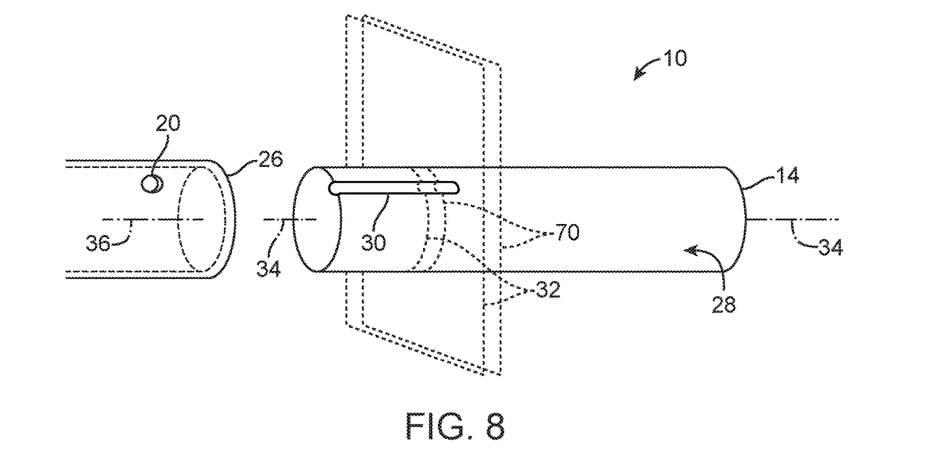
FIG. 8 is an isometric, exploded view showing an exemplary support tool having a groove depression intersected by a first transverse imaginary plane and a second transverse imaginary plane.

In FIGS. 1-3, depression 30 in curved outer surface 28 of support tool 14 includes wall 44 that forms a circle. The depression in FIGS. 1-3 can be referred to as circular depression 30. In further aspects of the invention, the depression in curved outer surface 28 of support tool 14 can take other shapes, such as an elongate groove as shown in FIG. 8. The depression in FIG. 8 can be referred to as groove depression 30.

In FIG. 8, groove depression 30 has transverse widths and radial depths that are uniform along the axial length of groove depression 30. First imaginary plane 32 and second imaginary plane 70 intersect depression 30. Planes 32 and 70 are transverse imaginary planes that are axially spaced apart from each other and are perpendicular to longitudinal central axis 34 of support tool 14 and/or longitudinal central axis 36 of endoprosthesis 26.

Figure 9:
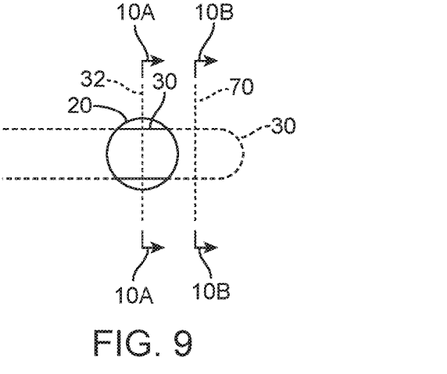
FIG. 9 is a partial plan view showing the groove depression of FIG. 8 positioned below the hole in the endoprosthesis.
Figure 10A:
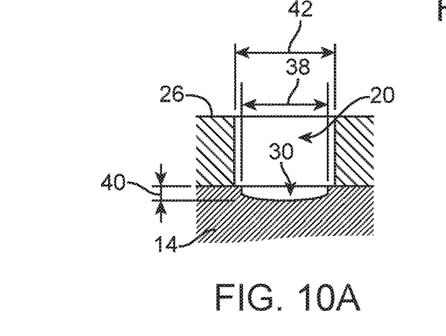
FIGS. 10A and 10B are fragmentary cross-section views at line 10A-10A and line 10B-10B of FIG. 9.
Figure 10B:
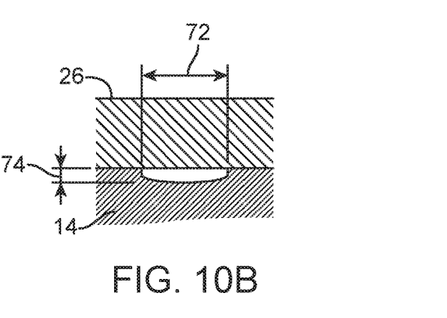

FIG. 9 shows a plan view of groove depression 30 of FIG. 8 after hole 20 of endoprosthesis 26 has been radially aligned above groove depression 30. FIGS. 10A and 10B show cross-section views of groove depression 30 at first imaginary plane 32 and second imaginary plane 70, respectively. FIG. 10A shows first width 38 and first radial depth 40 of groove depression 30 at first imaginary plane 32. FIG. 10B shows second width 72 and second radial depth 74 of groove depression 30 at second imaginary plane 70. First width 38 is equal to second width 72. First radial depth 40 is equal to second radial depth 74. Diameter 42 of hole 20 is greater than transverse widths 38 and 72 of groove depression 30.

Figure 11:
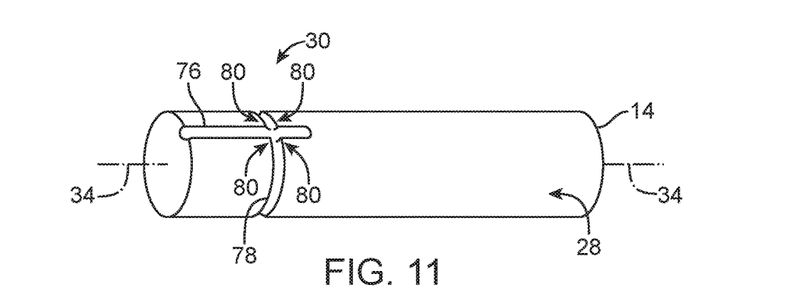
FIG. 11 is an isometric view showing an exemplary support tool having a depression formed by two intersecting grooves.

In further aspects of the invention, depression 30 in curved outer surface 28 of support tool 14 has the shape of a cross formed by two intersecting grooves 76 and 78 as shown in FIG. 11. Groove 76 extends axially and is the same as groove depression 30 of FIG. 8. Groove 78 extends in a traverse direction around the circumference of support tool 14. Groove 76 and groove 78 are mutually perpendicular and form corners 80 of curved outer surface 28 where the grooves intersect.

Figure 12:
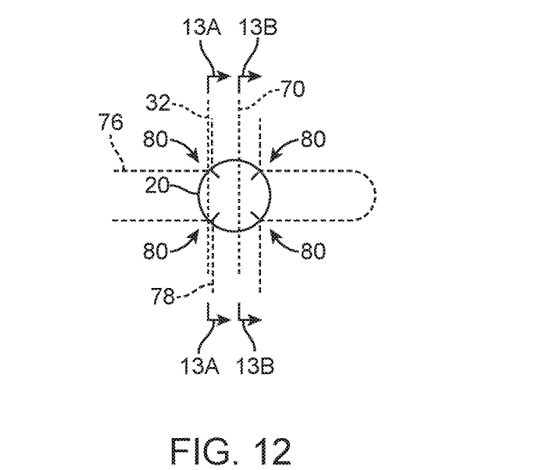
FIG. 12 is a partial plan view showing the depression of FIG. 11 positioned below the hole in the endoprosthesis.

FIG. 12 shows a plan view of depression 30 of FIG. 11 after hole 20 of endoprosthesis 26 has been radially aligned above the intersection of grooves 76 and 78. Corners 80 of curved outer surface 28 support endoprosthesis 26 to inhibit collapse of portions of endoprosthesis 26 adjacent to hole 20 during insertion of radiopaque marker bead 18 into hole 20.

Figure 13A:
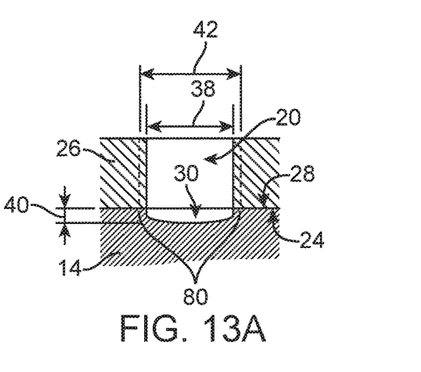
FIGS. 13A and 13B are fragmentary cross-section views at line 13A-13A and line 13B-13B of FIG. 12.
Figure 13B:
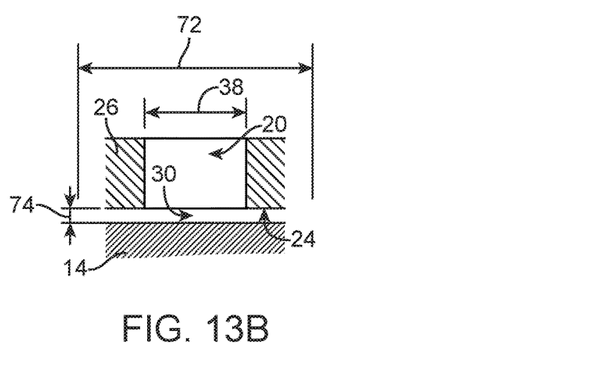

FIGS. 13A and 13B show cross-section views of depression 30 of FIGS. 11 and 12 at first imaginary plane 32 and second imaginary plane 70, respectively. FIG. 13A shows first width 38 and first radial depth 40 of depression 30 at first imaginary plane 32. FIG. 13B shows second width 72 and second radial depth 74 of depression 30 at second imaginary plane 70. First width 38 is less than second width 72. Diameter 42 of hole 20 is greater than first width 38 and less than second width 72. First radial depth 40 is equal to second radial depth 74.

In further aspects of the invention, the depression in curved outer surface 28 of support tool 14 can be a groove depression having variable widths and radial depths. The widths and/or radial depths may vary along the axial length of the groove, as will be described below. Variable dimensions of depression 30 can allow support tool 14 to be used with various diameters of hole 20. Variations in the diameter of hole 20 may be unintentional. For example, the hole diameter variation can due to random manufacturing variations. Variations in the diameter of hole 20 may be intentional. For example, the diameter of hole 20 for one type or size of endoprosthesis may, due to clinical or other reasons, need to be larger or smaller than that of another type or size of endoprosthesis.

Figure 14:
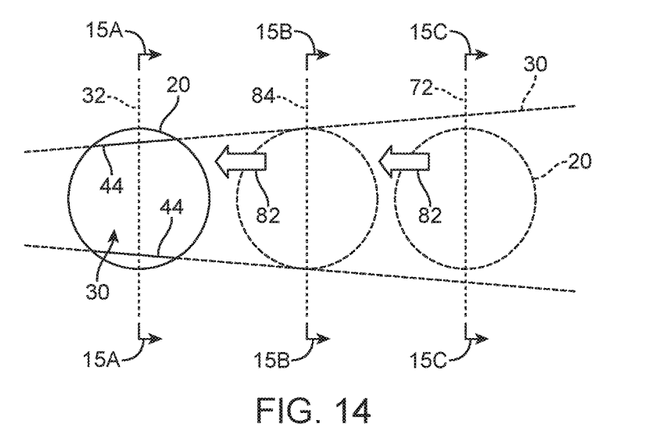
FIG. 14 is a partial plan view of an exemplary depression having widths that vary in size to accommodate varying sizes of radiopaque marker beads and varying diameters of the hole in the endoprosthesis.

FIG. 14 is a plan view of depression 30 having variable widths. The plan view shows depression 30 after support tool 14 has been inserted into endoprosthesis 26. In use, a person or mechanism can move support tool 14 and endoprosthesis 26 relative to each other until hole 20 is at a location over depression 30 that provides adequate support to luminal surface 24 of endoprosthesis 26. For example, endoprosthesis can be moved in the direction of arrow 82 until walls 44 of depression 30 are visible through hole 20 in the endoprosthesis. When walls 44 become visible, the diameter of hole 20 will be slightly greater than the width of depression 30 at that location, similar to the condition described for FIGS. 9 and 10A. In other aspects, the support tool is moved, while the endoprosthesis remains stationary, until walls 44 of depression 30 are visible through hole 20 in the endoprosthesis.

First imaginary plane 32 and second imaginary plane 70 intersect depression 30. In addition, third imaginary plane 84 intersects depression 30 and is disposed between the first and second imaginary planes. Planes 32, 70, and 82 are all transverse imaginary planes like pane 32 in FIG. 6. In other aspects, planes 32, 70, and 82 are all axial imaginary planes like plane 32 in FIG. 1.

Figure 15A:
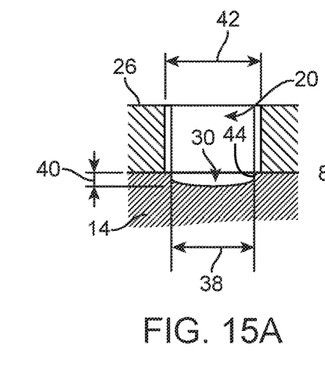
FIGS. 15A, 15B, and 15C are fragmentary cross-section views at line 15A-15A, line 15B-15B, and line 15C-15C of FIG. 14.

FIG. 15A is a cross-section view of groove depression 30 at first imaginary plane 32 of FIG. 14. At first imaginary plane 32, groove 30 has first width 38 and first radial depth 40. First width 38 is less than diameter 42 of hole 20 in endoprosthesis 26.

Figure 15B:
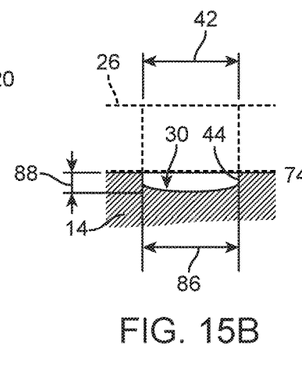
Figure 15C:
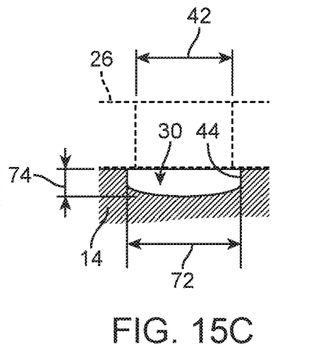

FIG. 15C is a cross-section view of depression 30 at second imaginary plane 72. At second imaginary plane 72, depression 30 has second width 72 and second radial depth 74. Second width 72 is greater than first width 38 and greater than diameter 42 of hole 20 in endoprosthesis 26. Second radial depth 74 is greater than first radial depth 40. In some aspects, insertion of radiopaque marker bead 18 is performed while hole 20 in endoprosthesis 26 is positioned over this area of support tool 14.

FIG. 15B is a cross-section view of depression 30 at third imaginary plane 84. At third imaginary plane 84, depression 30 has third width 86 and third radial depth 88. Second width 72 is equal to diameter 42 of hole 20 in endoprosthesis 26. Third radial depth 88 is greater than first radial depth 40 and less than second radial depth 74. In some aspects, insertion of radiopaque marker bead 18 is performed while hole 20 in endoprosthesis 26 is positioned over this area of support tool 14.

In other aspects of the invention, radial depths of depression 30 of FIG. 14 do not vary. Radial depths 40, 74, and 88 are equal, and widths 38, 72, and 86 differ from each other as described above.

In further aspects of the invention, radiopaque marker bead 18 can have a diameter, prior to being pushed into hole 20, that is equal to diameter 42 of hole 20 in endoprosthesis 26. The diameter of radiopaque marker bead 18 prior to being pushed into hole 20 is referred to as an initial diameter. In other aspects, radiopaque marker bead 18 can have an initial diameter that is within the range of 80% to 120% of diameter 42 of hole 20 in endoprosthesis. When radiopaque marker bead 18 is smaller in diameter than hole 20, pressing opposite ends radiopaque marker bead 18 as described above can help to ensure that radiopaque marker bead 18 engages the walls of hole 20. When radiopaque marker bead 18 is greater in diameter than hole 20, the walls of hole 20 may expand or deform slightly to accommodate radiopaque marker bead 18, and pressing opposite ends radiopaque marker bead 18 as described above can help minimize the extent to which radiopaque marker bead 18 protrudes out of the abluminal and luminal surfaces of the endoprosthesis.

Figure 16A:
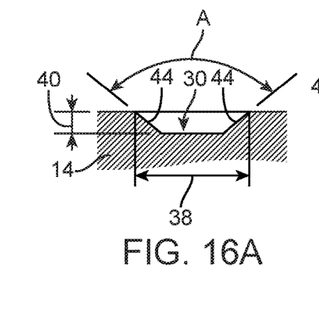
FIGS. 16A, 16B, and 16C are fragmentary cross-section views of exemplary depressions each having non-parallel side walls.
Figure 16B:
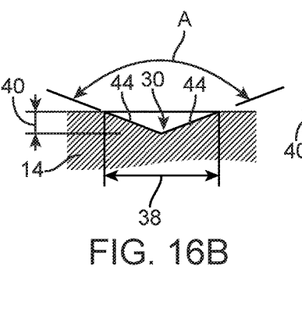
Figure 16C:
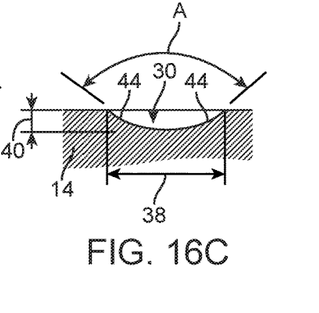

In aspects of the invention, side walls 44 of depression 30 are parallel to each other when viewed in cross-section. See, for example, FIGS. 2, 7, and 15A which show parallel side walls 44 in cross-section. In further aspects of the invention, side walls 44 when viewed in cross-section (in axial cross-section like FIG. 2 or in transverse cross-section like FIG. 7) are not parallel to each other. For example, as shown in FIGS. 16A-16C, side walls 44 when viewed in cross-section can be sloped so as to be at an interior angle A to each other.

Angle A can be at least 60 degrees or at least 90 degrees. In further aspects, angle A can be from 60 degrees to 150 degrees, or from 90 degrees to 150 degrees. After pressing of first portion 50 of radiopaque marker bead 18, support tool 14 can be rotated about its longitudinal central axis 34 and/or longitudinal central axis 36 of endoprosthesis 26, as mentioned above. Side walls 44 that are at an angle A relative to each other can allow rotation of support tool 14 to adequately flatten second portion 52 and cause second portion 52 to fill in luminal end segment 48 of hole 20.

Figures 17A, 17B:
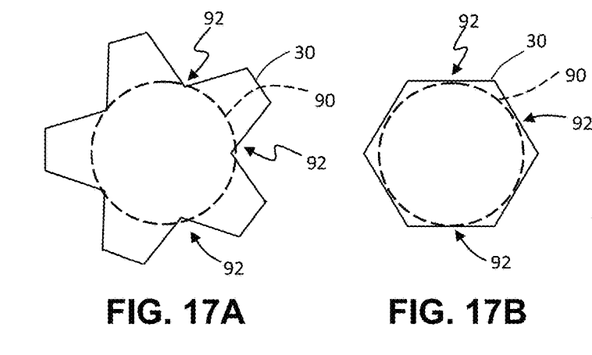
FIGS. 17A, 17B, and 17C are plan views of exemplary depressions with different shapes.
Figure 17C:
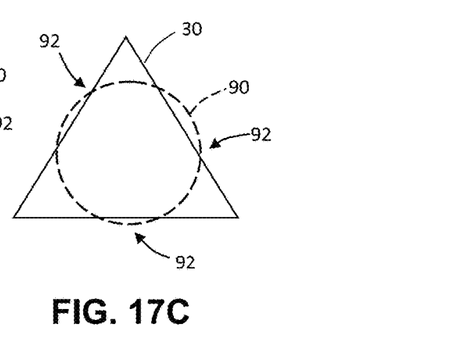

In aspects of the invention, depression 30 can be an elongate groove. See for example FIGS. 8 and 9 which show groove depression 30. In further aspects of the invention, depression 30 when seen in plan view has the shape of a star as shown in FIG. 17A or a polygon as shown in FIGS. 17B and 17C. In FIGS. 17A-17C, broken line 90 represents wall 62 of hole 20 in endoprosthesis 26 and/or the outer surface of radiopaque marker bead 18 before being pushed into hole 20. As compared to circular depression 30 of FIG. 3, depressions 30 of FIGS. 17A-17C have the advantage of providing multiple support points 90 to the luminal surface around hole 20 in the endoprosthesis with a lower chance of obstructing entry of radiopaque marker bead 18 into depression 30.

As indicated above, endoprosthesis 26 can be a stent. FIG. 18A shows an exemplary bioresorbable stent 26 to which radiopaque marker beads 18 have been attached. FIG. 18B shows a detail view of an end segment of stent 26. Stent 26 is designed to be delivered through an anatomical lumen using a catheter and subsequently expanded. Stent 26 has a cylindrical shape having central axis 36 and includes a pattern of interconnecting structural elements known as struts 114. Axis 36 extends through the center of the cylindrical shape formed by struts 114. The stresses involved during compression and deployment are generally distributed throughout various struts 114 but are concentrated at the bending elements or strut junctions.

There are different types of struts 114. Struts 114 include a series of ring struts 116 that are connected to each other by bending elements 118. Ring struts 116 and bending elements 118 form sinusoidal rings 120 configured to be reduced and expanded in diameter. Rings 120 are arranged longitudinally and centered on axis 36. Struts 114 also include link struts 122 that connect rings 120 to each other. Rings 120 and link struts 122 collectively form a tubular scaffold of stent 26. Abluminal surface 22 is visible in the foreground. Luminal surface 24 is visible in the background. Holes 20 are formed through one of the link struts. In other aspects, holes 20 can be formed through any of the other struts 114. Radiopaque marker beads 18 are attached to stent 26.

In aspects of the invention, the core substrate of endoprosthesis 26 can be made of a biostable polymer material or a bioresorbable polymer material. The bioresorbable polymer material can be a material selected from the group consisting of poly(L-lactide) ("PLLA"), poly(L-lactide-co-glycolide) ("PLGA"), poly(D,L-lactide-co-glycolide), poly(L-lactide-co-caprolactone), poly(glycolide-co-caprolactone) and poly(L-lactide-co-D-lactide) ("PLLA-co-PDLA"). Examples of polymers for the core substrate material include without limitation the polymers described in U.S. Pat. No. 8,002,817.

In aspects of the invention, radiopaque marker bead 18 is made of a material that is more radiopaque than the core substrate material of endoprosthesis 26. Methods for qualitative and quantitative comparison of the radiopacity of radiopaque marker bead 18 versus that of the core substrate material of endoprosthesis 26 can be developed with reference to ASTM F640-12, "Standard Test Methods for Determining Radiopacity for Medical Use," which is incorporated herein by reference in its entirety.

In aspects of the invention, radiopaque marker bead 18 includes, consists essentially of, or consists of any of platinum and iridium. Radiopaque marker bead 18 may include, consists essentially of, or consists of platinum, iridium, cobalt chromium alloy, stainless steel (e.g., 316L), high nitrogen stainless steel, Nitinol, tantalum, nickel, tungsten, titanium, gold, magnesium, or an alloy or combination of any two or more thereof.

In aspects of the invention, any of pusher tool 12, support tool 14, and tool 66 can be made of a material having a greater hardness than radiopaque marker bead 18 and the core substrate of endoprosthesis 26. In further aspects, any of pusher tool 12, support tool 14, and tool 66 can be made of metal, including without limitation stainless steel.

Figure 19:
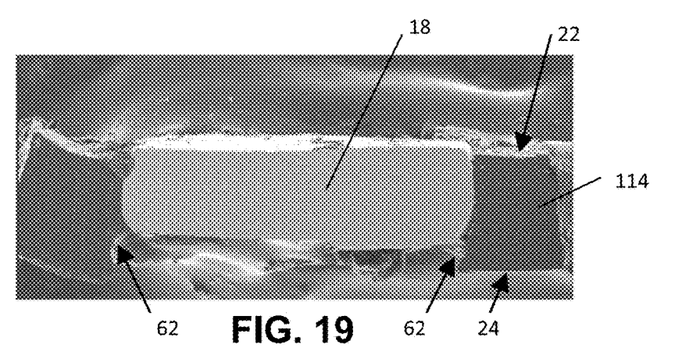
FIG. 19 is an image from a scanning electron microscope, showing a cross-section of a stent strut with a radiopaque marker bead attached to the stent strut using a support tool having no depression.

In FIG. 19, a scanning electron micrograph shows a radiopaque marker bead that was pressed into a hole in a stent strut. A support tool which had no depression was used to support luminal surface 24 of stent strut 114. When radiopaque marker bead 18 was pressed in the hole, the malleable radiopaque material accumulated at the abluminal end segment of the hole before radiopaque marker bead 18 adequately entered the hole. This is evident from the presence of radiopaque marker bead material protruding above abluminal surface 22 of stent strut 114. Also, radiopaque marker bead 18 did not fill the luminal end segment of the hole. This is evident from the difference in elevation between radiopaque marker bead 18 and luminal surface 24. Significant portions of wall 62 of the hole are not frictionally engaged by radiopaque marker bead 18.

Figure 20:
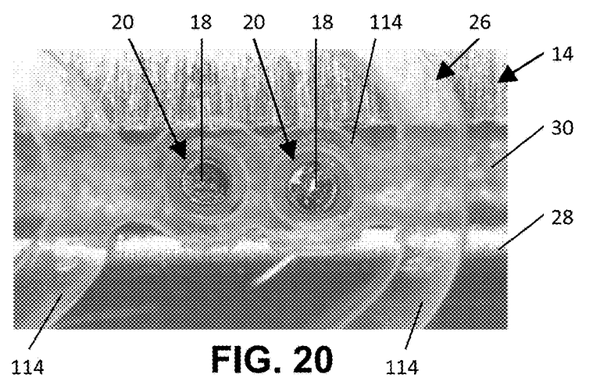
FIG. 20 is a photograph showing a plan view of radiopaque marker beads pressed into holes in a stent strut supported by a support tool with a groove.

In FIG. 20, radiopaque marker beads 18 have been pressed into holes 20 in stent strut 114 of endoprosthesis 26 made of a bioresorbable polymer. Stent struts 114, which appear translucent, are supported from below by support tool 14 made of metal. Holes 20 are radially aligned above groove depression 30 into curved outer surface 28 of support tool 14.

Figure 21:
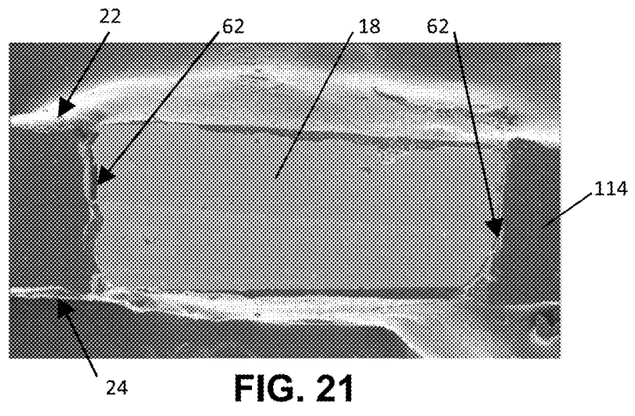
FIG. 21 is an image from a scanning electron microscope, showing a cross-section of a stent strut with a radiopaque marker bead attached to the stent strut using a support tool with a depression.

In FIG. 21, a scanning electron micrograph shows a radiopaque marker bead that was pressed into a hole in a stent strut. In this case, a support tool which had a depression was used to support luminal surface 24 of the stent strut. Radiopaque marker bead 18 filled both the abluminal and luminal end segments of the hole. Virtually all portions of wall 62 of the hole are frictionally engaged by radiopaque marker bead 18. Engagement of both end segments of hole 20 can be preferable in that radiopaque marker bead 18 would be expected to have a lower chance of become dislodged and separated from the endoprosthesis as compared to radiopaque marker bead 18 of FIG. 19.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for attaching a radiopaque marker bead to an endoprosthesis, the method comprising:

positioning the radiopaque marker bead adjacent to the endoprosthesis such that a first portion and a second portion of the radiopaque marker bead are disposed over a hole formed through an abluminal surface of the endoprosthesis;

after positioning, pressing the first portion of the radiopaque marker bead into the hole until the second portion of the radiopaque marker bead moves out of the hole and protrudes from a luminal surface of the endoprosthesis;

supporting the luminal surface of the endoprosthesis with a curved outer surface of a support tool, wherein a depression is formed into the curved outer surface, the depression is radially aligned with the hole formed in the endoprosthesis, and the supporting is performed simultaneous with pressing the first portion of the radiopaque marker bead; and after pressing the first portion, pressing the second portion of the marker into the hole.

2. The method of claim 1, wherein pressing the second portion is performed by rotating the support tool.

3. The method of claim 1, wherein the depression in the curved outer surface of the support tool receives the second portion of the radiopaque marker bead when the first portion of the radiopaque marker bead is pressed into the hole, and the depression has a radial depth that limits travel of the second portion out of the hole.

4. The method of claim 1, further comprising inserting the support tool into the endoprosthesis such that the curved outer surface of the support tool supports the luminal surface of the endoprosthesis, wherein the inserting is performed before pressing the first portion of the radiopaque marker bead.

5. The method of claim 4, further comprising removing the support tool from the endoprosthesis, the removing performed before or during pressing the second portion of the radiopaque marker bead.

6. The method of claim 1, wherein pressing the first portion of the radiopaque marker bead includes flattening the first portion.

7. The method of claim 1, wherein pressing the first portion of the radiopaque marker bead includes deforming the first portion to fill an abluminal end segment of the hole with the first portion.

8. The method of claim 1, wherein pressing the second portion of the radiopaque marker bead includes flattening the second portion.

9. The method of claim 1, wherein pressing the second portion includes deforming the second portion to fill a luminal end segment of the hole with the second portion of the radiopaque marker bead.

10. The method of claim 1, wherein the radiopaque marker bead is spherical before pressing the first portion, and the radiopaque marker bead is a disc after pressing the second portion.

* * * * *